(12) United States Patent
Greene

(10) Patent No.: US 7,645,608 B2
(45) Date of Patent: Jan. 12, 2010

(54) MICROORGANISM SPECIMEN STORAGE, HYDRATING, TRANSFER AND APPLICATOR DEVICE

(75) Inventor: Nathan Greene, Thousand Oaks, CA (US)

(73) Assignee: PML Microbiologicals, Inc., Wilsonville, OR (US)

( * ) Notice: Subject to any disclaimer, the term of this patent is extended or adjusted under 35 U.S.C. 154(b) by 219 days.

(21) Appl. No.: 11/203,929

(22) Filed: Aug. 15, 2005

(65) Prior Publication Data

US 2006/0040340 A1 Feb. 23, 2006

Related U.S. Application Data

(60) Provisional application No. 60/601,973, filed on Aug. 17, 2004.

(51) Int. Cl.
*C12M 1/26* (2006.01)
*C12M 1/36* (2006.01)
*C12M 3/00* (2006.01)

(52) U.S. Cl. .............. 435/286.3; 435/309.1; 435/309.2; 435/810

(58) Field of Classification Search .................. None
See application file for complete search history.

(56) References Cited

U.S. PATENT DOCUMENTS

| | | | |
|---|---|---|---|
| 3,450,129 A | 6/1969 | Avery et al. | |
| 3,671,400 A | 6/1972 | Cekoric, Jr. et al. | |
| 4,175,008 A | 11/1979 | White | |
| 4,311,792 A | 1/1982 | Avery | |
| 4,353,868 A | 10/1982 | Joslin et al. | |
| 4,615,823 A | 10/1986 | Tokuyama et al. | |
| 4,749,655 A | 6/1988 | Monthony et al. | |
| 4,978,504 A | 12/1990 | Nason | |
| 5,078,968 A | 1/1992 | Nason | |
| 5,114,003 A | 5/1992 | Jackisch et al. | |
| 5,155,039 A | 10/1992 | Chrisope et al. | |
| 5,238,649 A | 8/1993 | Nason | |
| 5,266,266 A | 11/1993 | Nason | |
| 5,279,964 A | 1/1994 | Chrisope | |
| 5,856,172 A | 1/1999 | Greenwood et al. | |
| 5,879,635 A | 3/1999 | Nason | |

FOREIGN PATENT DOCUMENTS

WO    WO 97/15331    5/1997

*Primary Examiner*—David M. Naff
*Assistant Examiner*—Deborah K. Ware
(74) *Attorney, Agent, or Firm*—Chernoff Vilhauer McClung & Stenzel, LLP

(57) ABSTRACT

A device for storing, rehydrating, transferring, and streaking a stored freeze dried specimen comprises a three piece construction including a collection vial used to store a freeze dried specimen, a capsule including a reservoir with hydrating fluid retained by a frangible membrane, and an adapter fluidly linking the capsule to the collection vial. The adapter is configured to fluidly link to the capsule to the collection vial via leak-proof couplings to create a closed system of specimen, hydrating fluid, and a small quantity of trapped air. The fluid communication between the vial and the capsule is accomplished through the adapter via an internal lumen longitudinally traversing the adapter. The adapter and capsule combination can also serve as a transfer pipette once the hydration operation is complete to withdraw the specimen from the collection vial and transfer the specimen to a petri dish or other culture medium. The adapter and capsule combination is quickly detachable from the collection vial to allow an inoculating tip exposed to the specimen to be transferred conveniently to a media for culturing with minimal exposure. The inoculating tip is also capable of streaking the transferred specimen to create isolated colonies in the medium from the transferred specimen.

5 Claims, 1 Drawing Sheet

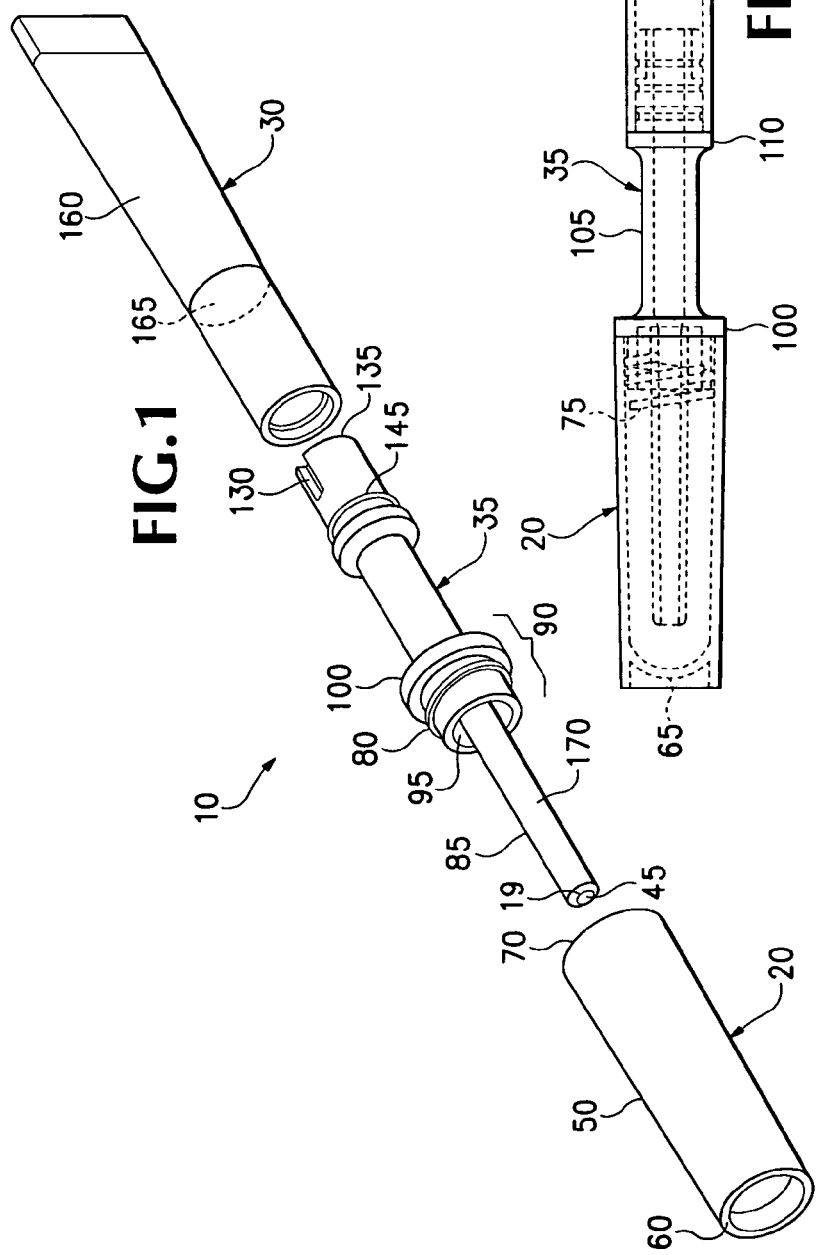
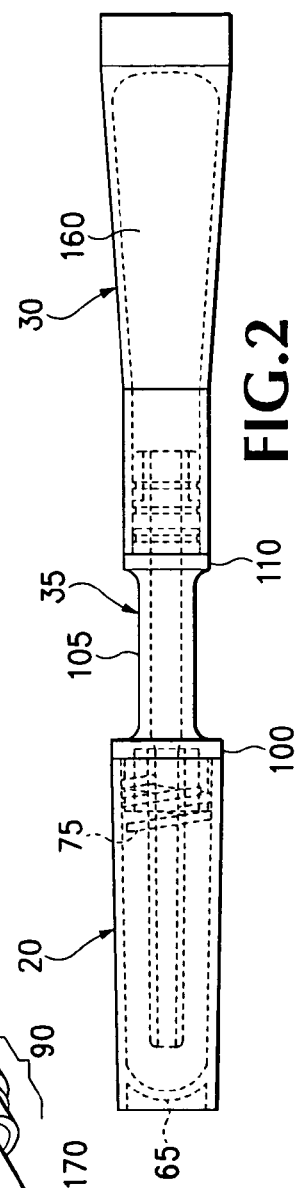
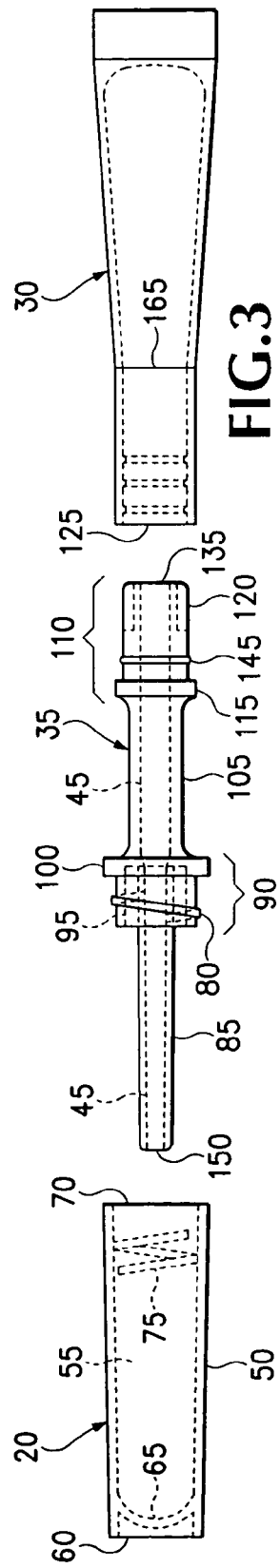

MICROORGANISM SPECIMEN STORAGE, HYDRATING, TRANSFER AND APPLICATOR DEVICE

CROSS-REFERENCE TO RELATED APPLICATIONS

This application claims priority of U.S. Application No. 60/601,973, filed Aug. 17, 2004.

BACKGROUND OF THE INVENTION

The field of the invention relates to the culturing of microorganism samples, and more particularly to a three-piece all-in-one device that stores, rehydrates, and extracts, transfers, and streaks a microorganism sample in a sterile environment without the need for additional implements such as transfer pipettes or inoculation loops, with the goal of achieving isolated colonies of cultured microorganism growth in a nutrient-rich environment.

Laboratory professionals use known freeze-dried microorganisms to validate test procedures and laboratory results. These known microorganisms, for example *Escherichia coli*, have distinct growth characteristics and reactions to biochemicals. Such microorganisms are commercially available to laboratories that perform microbiology testing. Diagnostic testing systems rely on the distinct growth characteristics and reactions of such microorganisms.

A procedure has been developed whereby a known microorganism is isolated, freeze-dried, and stored in a sterile vial for later use. In order to validate test procedures and/or laboratory results, a laboratory professional rehydrates the microorganism from its freeze-dried state by adding a sterile liquid to create a suspension containing the microorganism. A sample of the suspension is extracted and transferred to a Petri dish for culturing in order to grow colonies of the microorganism. The isolated colonies are then examined to compare their growth and response to biochemicals to known characteristics of the microorganism.

The foregoing hydration procedure requires adding the sterile freeze-dried microorganism to a sterile solution by introducing a measured quantity of hydrating fluid and agitating the solution. The addition of the hydrating solution is typically accomplished with a transfer pipette, which must be sterile to avoid contaminating the specimen. In some cases, the pipette is used to mix the solution. In others the solution may be capped in a vial and mixed to ensure complete rehydration. Care must be taken that the cap (if the original storage container is used) or the new container (if mixed separately from the original storage container) is also sterile to avoid contamination during mixing. Then, a new pipette or inoculation loop is used to extract a quantity of the solution containing the rehydrated microorganism to a nutrient-enriched medium such as agar, so that the microorganism can be cultured under controlled conditions.

A crucial step in the culturing process is the inoculation of the agar with the specimen in a manner so as to create isolated colonies so a microbiologist can observe the microorganism's morphology. Using a technique referred to a "streaking," an inoculation device having an inoculating end, such as a loop, is typically used to spread the specimen across the surface of the agar. Typically, the Petri dish is divided into four quadrants and the microorganism suspension is placed in the first quadrant and streaked side to side. The procedure is repeated for quadrants two, three and four, with each successive quadrant reflecting diminished concentrations of the solution, to yield isolated colonies of microorganism after culturing.

The use of an inoculation loop facilitates the creation of individual colonies, which are otherwise difficult to achieve without a specialized inoculating wand. This allows the microbiologist or laboratory technician to view the morphology of the microorganism to ensure purity of the culture. The incubation period, depending on the rate of growth of the microorganism, can typically be 24 hours or longer. If the inoculation has been performed correctly and without contamination, individual colonies of microorganism may be identified, studied and compared to known results.

The foregoing prior art process is rife with opportunities for contamination that can foil the testing process and lead to false results. Contamination opportunities exist when the specimen is first exposed to airborne contaminants during the rehydration step, or to contaminated transfer pipettes or to mixing containers. Contaminated rehydrating fluid also poses an opportunity for contamination of the culture. Next, mixing in a vial introduces the potential for contamination, as the solution contacts new surfaces when the solution is shaken, stirred, or otherwise mixed. The transfer of the rehydrated specimen to a culture dish with a transfer pipette presents yet another opportunity for contaminating the specimen. Finally, the streaking of the specimen in the dish with an inoculating loop or other implement presents yet another opportunity for contamination.

The use of plastic inoculation loops and plastic transfer pipettes represents an advance over metal counterparts in decreased manufacturing costs at the expense of new sterilization problems. Heat sterilization over an open flame was used to sterilize the metal inoculation loops and glass pipettes, but this form of sterilization is unavailable when using plastic counterparts for obvious reasons. Therefore, inoculation loops and transfer pipettes must be sterilized by other means such as irradiation, electron beam, or autoclaving before packaging. However, contamination is still a constant threat because the slightest contact with any non-sterile surface, even removing the inoculating loop or transfer pipette from its packaging, can contaminate the specimen. Because the incubation period can be a day or more, the time before it may be discovered that contamination has occurred leads to inefficiency, undue delay, and frustration of the microbiologist or laboratory technician if the entire procedure must be repeated.

In addition to the constant threat of contamination, the inconvenience of stocking each separate implement used in the process is evident. Each testing requires a separate storage container, a separate sterile mixing container, a sterile transfer pipette or other sterile transfer device, and a sterile inoculation loop or other inoculation device for streaking the specimen. There is therefore a need in the art for a convenient, all-in-one storage, hydration, transfer, and streaking device that minimizes the risk of contamination in the various stages of the bacterial growth testing.

SUMMARY OF THE INVENTION

The present invention provides an all-in-one storage, hydration, and inoculation device that reduces the possibility of contamination by eliminating the need for extraneous transfer pipettes and inoculation loops. The present invention comprises a three-piece device that includes a collection vial for storing a freeze-dried microorganism specimen, an interlocking adapter that serves as both a transfer pipette and an inoculation device, and a detachable capsule for hydrating the freeze-dried specimen. The capsule includes a liquid reservoir with a frangible membrane that, when ruptured, can deliver hydrating fluid to the stored, dry specimen through an internal lumen in the adapter. The internal lumen permits hydration of the specimen while the adapter is connected to the collection vial, whereupon the adapter and capsule combination can be used in place of a transfer pipette to extract a quantity of the hydrated specimen from the collection vial without exposing the adapter, collection vial, or the hydrated solution to the outside environment. With the specimen collected in the adapter, the collection vial is removed and the specimen is deposited on an agar medium. The inoculating tip is formed as an integral part of the interlocking adapter so as to serve as an inoculation applicator in place of an inoculating loop to streak the specimen and create isolated colonies of the cultured specimen.

The all-in-one device featuring an adapter, a vial, and a rehydrating capsule greatly reduces the opportunity for contamination because the unit can be sterilized first, and then assembled with the freeze-dried sample included in the vial. Because the rehydration, mixing, and transfer occur while the unit is assembled, external contamination is eliminated. Further, by using the inoculating applicator to immediately streak the specimen, no new implements are introduced and the opportunity for contamination is minimized. The inventive device is also far more convenient than prior art devices because it accomplishes storing, hydrating, extracting, and streaking a microorganism specimen with a single, cost-effective unit. Other features and advantages of the invention will become apparent from the following detailed description, taken in conjunction with the accompanying drawings which illustrate, by way of example, the features of the invention The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

FIG. 1 is a perspective exploded view of a preferred embodiment of the present invention;

FIG. 2 is an elevational view of the embodiment shown in FIG. 1; and

FIG. 3 is an exploded elevational view of the embodiment shown in FIG. 1.

DETAILED DESCRIPTION OF PREFERRED EMBODIMENTS

FIGS. 1-3 illustrate a preferred embodiment of the invention comprising three interlocking elements cooperating to form an all-in-one microorganism specimen storage, hydrating, transfer, and streaking device 10. The three elements include collection vial 20, fluid-releasing capsule 30 for hydrating a dried specimen, and adapter 35 with a lumen 45 capable of fluidly connecting collection vial 20 to capsule 30. Collection vial 20 stores the freeze-dried microorganism specimen (not shown) in a sterile environment until the specimen is needed for testing, and is a cylinder with a wall 50 forming an elongate cavity 55 therein. At a distal end 60 of collection vial 20 is concave bottom 65 that is slightly recessed. The opposite end 70 of collection vial 20 is open, and includes threads 75 on an interior surface that engage threads 80 on an outer surface of adapter 35 to form a fluid-tight seal with the adapter 35, and can be quickly and easily disengaged from the adapter by disengaging the mating threads.

Adapter 35 includes an elongate inoculating applicator tip 85 extending longitudinally into collection vial 20. Adapter 35 is preferably formed with injection molding to form an integral structure having a plurality of radial dimensions along its longitudinal axis. Inoculating tip 85 may have a length of 1.345 inches and an outer diameter of 0.15 inch. The radius of the corner at the rounded opening 19 of inoculating tip 85 is preferably 0.035 inch, and the annular thickness of the tip 85 at the opening 19 is preferably 0.142 inch. The dimension of the inoculating tip, and particularly the contact surface, have been experimentally determined to be especially effective in achieving isolated colonies of bacterial samples when inoculating tip 85 is used to streak the bacterial specimen in an agar Petri dish.

Adapter 35 includes an integral stopper 90 at an intermediate location that is sized to fit into and plug the open end 70 of collection vial 20, and positioned to extend inoculation tip 85 substantially into collection vial 20 when the stopper is engaged therewith. Stopper 90 comprises an annular rim 95 extending from a disk-shaped cap 100, where annular rim 95 includes threads 80 on its outer surface for engaging the threads 75 on collection vial 20 to sealingly close collection vial 20.

As best seen in FIG. 2, inoculating tip 85 extends from cap 100 to a position just above the concave bottom 65 of collection vial 20 when the unit is assembled. Adjacent stopper 90 is a neck portion 105 comprising a substantially cylindrical wall having an outer diameter of 0.25 inch and a length approximately 0.75 inch. Neck portion 105 is bordered by disk-shaped cap 100 on a first side, and plug 110 on the second side.

Plug 110, like stopper 90 at the opposite end, has a disk-shaped cap 115 extending radially outward from the surface of the adapter and an annular extension 120 sized to be received in the socket 125 of hydrating capsule 30. Annular extension 120 may include longitudinal slots 130 at diametrically opposed positions extending from a proximal end 135 of the extension 120 to approximately a midpoint thereof, which may receive inwardly projecting guides (not shown) disposed on an interior surface of said socket 125 of the hydrating capsule 30 to position and secure together adapter 35 and capsule 30. Circumferential ridge 145 on the outer surface of plug extension 120 further assists in securing the plug in place and acts as a seal to ensure a solid, fluid-tight connection.

Adapter 35 further includes a lumen 45 extending completely through from the distal end 150 of inoculating tip 85 to the proximal end 135 of the extension of the plug, forming a continuous fluid channel therethrough. In a preferred embodiment, the lumen 0.24 inch at the annular extension 120 and 0.079 inch at opening 19 of inoculating tip 85.

Capsule 30 is a plastic tubular structure divided into two compartments. The top compartment comprises a hydrating liquid-filled compressible reservoir 160 isolated from the bottom compartment of the capsule by a frangible membrane 165 serving as an internal wall. No glass is used for the reservoir 160, eliminating the shortcomings associated with glass ampoules and glass fragments or shards contaminating the specimen. The hydrating liquid can be sterile water, but alternatively can be any hydrating or wetting agent that suits the particular needs of the specimen to be tested. Frangible membrane 165 is pressure-sensitive in that either a directly applied compressive force or a sufficient increase in the pressure on the membrane will cause the membrane to tear or rupture, thereby allowing the hydrating fluid to evacuate of reservoir 160, as the reservoir expands it fills with air enclosed in the device such as the air trapped in lumen 45 and collection vial 20.

The bottom compartment of capsule 30 on the other side of the membrane 165 is provided with socket 125 for coupling plug 110 to adapter 35. Socket 125 is a cylindrical structure that may include guides (not shown) longitudinally disposed on opposite sides for engaging slots 130 on plug extension 120. In a preferred embodiment, capsule 30 can include a pad or mark at the membrane that can be used to show the position of membrane 165, allowing the user to apply lateral force directly to the membrane, causing it to break or rupture. Alternatively, fluid reservoir 160 can be compressed to increase the internal pressure until membrane 165 ruptures, causing the fluid to be expelled into the socket.

In practice, a bacterial specimen is placed in the sterilized collection vial 20 for storage, and sterilized adapter 35 is connected to the collection vial 20 where the threads 80 on stopper 90 engage threads 75 on the internal surface of the collection vial, thereby sealing the vial. The bacterial specimen is then freeze-dried inside the vial. With the freeze-dried specimen in collection vial 20 and adapter 35 extending therefrom, sterilized capsule 30 containing sterilized hydrating fluid is placed on the opposite end 135 of adapter 35 by aligning the guides with slots 130 on plug extension 135, and then plug 110 is inserted into socket 125 of capsule 30, thereby forming another seal. Lumen 45 on adapter 35 connects collection vial 20 to the port of capsule 30 at the end of the socket 125, but no fluid is conveyed as long as frangible membrane 165 is intact, making the device a closed system relative to the outside environment. FIG. 2 shows the fully assembled device 10. With the freeze-dried specimen stored in the collection vial the device can be transported and stored for long periods of time with minimal risk of contamination as the specimen is sealed in a tight and moisture-resistant storage arrangement.

When the time comes for the microbiologist or lab technician to test the bacterial or other microorganism specimen in a controlled environment, device 10 is preferably placed upright so that capsule 30 is on top and collection vial 20 containing the specimen is on the bottom. With the thumb and forefinger placed on neck 105 of adapter 35 for support, fluid reservoir 160 is compressed in the area of the frangible adapter 35 for support, fluid reservoir 160 is compressed in the area of the frangible membrane 165, causing it to break. Sterile fluid in the reservoir 160 is then expelled by pressure of the compressed reservoir and by gravity downward, evacuating the reservoir. The fluid travels across the membrane 165, through socket 125, and out the socket's port. Because the connection between capsule 30 and adapter 35 is fluid-tight, the fluid continues its downward travel by gravity and pressure to plug 110 of adapter 35 and is forced through internal lumen 45 and into collection vial 20, thereby hydrating the specimen. Because adapter 35 and collection vial 20 form a sealed coupling, the specimen and hydrating fluid can be mixed without disengaging the adapter so as to ensure that the freeze-dried specimen is hydrated in a sterile environment.

With the rehydrated bacterial specimen in the collection vial, device 10 can be used like a transfer pipette to extract the specimen back through lumen 45 by compressing fluid reservoir 160 to expel the air therein, and then releasing the compressed reservoir, whereby the expansion of the reservoir walls creates a vacuum that draws the solution of bacterial specimen and hydrating fluid back into the adapter and the capsule. This rehydrating and extraction of the specimen occurs within the closed environment of the device without exposing the specimen to the external environment. With the specimen now collected in the adapter and capsule combination, the collection vial is disconnected from the adapter by relative twisting rotation of the coupling threads to release the adapter and capsule combination from the collection vial. Inoculation is accomplished when the specimen is then transferred to a culture medium such as an agar-filled Petri dish by holding the adapter/capsule combination over the Petri dish and gently compressing the fluid reservoir to expel a predetermined quantity of the solution onto the agar.

Having inoculated the Petri dish with the specimen, the applicator may then also serve as a streaking device. Using inoculating tip 85 of adapter 35 to dispense the specimen at about a 45° angle relative to the surface of the dish, the specimen is streaked across the agar in a sinusoidal pattern while maintaining a continuous and unbroken streak of specimen from start to finish. Inoculating tip 85 is adapted with its particular dimensions at the contact surface to consistently form an uninterrupted streak of specimen, which in turn leads to a desired set of independent, isolated colonies of bacteria after culturing in the agar.

A clear benefit of the present invention is that the specimen can be stored in its freeze-dried state for extended periods of time, and then hydrated, mixed, extracted, transferred and streaked without exposure to any external environment and without the need for a separate transfer pipette or inoculating loop.

The foregoing has outlined in general the physical aspects of the invention and is to serve as an aid to understand the general principles of the invention. The present invention is not to be limited to any method or detail of the foregoing description, which is merely illustrative. Any variation of fabrication, use, or application as would be understood by one of ordinary skill in the art should be considered part of present invention.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A three-piece interlocking specimen storage, rehydrating, transfer, and streaking device comprising:
    a storage vial for storing a bacterial specimen having a cylindrical side wall with an open top end and a closed bottom end;
    a compressible hydrating capsule comprising a socket at a proximal end, and a sealed reservoir storing a rehydrating fluid at a distal end, said sealed reservoir having a frangible membrane retaining said rehydrating fluid therein; and
    an elongate adapter disposed between said hydrating capsule and said storage vial and adapted to be coupled to said storage vial and to said hydrating capsule in a fluid-tight relationship, said adapter including an internal, longitudinally extending lumen defining a fluid path between said rehydrating capsule and said storage vial, said adapter further comprising an elongate inoculating tip adapted to streak said specimen in a culturing medium
    wherein, after said frangible membrane is ruptured, and upon compression, said hydrating capsule is capable of withdrawing fluid from said storage vial through said lumens of said adapter and, upon further compression, is capable of expelling fluid through said lumens and out of said inoculating tip.

2. The device of claim 1 further comprising male threads on said adapter engaging complimentary female threads on said storage vial at said open top end to form a resealable engagement between said storage vial and said adapter.

3. The device of claim 1 wherein said inoculating tip has an outer diameter of 0.1".

4. The device of claim 1 wherein said inoculating tip has a rounded corner at a distal end with a radius of 0.035".

5. The device of claim 1 wherein said inoculating tip has an annular thickness of 0.142".

* * * * *